United States Patent
Hoof et al.

(10) Patent No.: US 8,968,374 B2
(45) Date of Patent: Mar. 3, 2015

(54) SELF-TAPPING BIOCOMPATIBLE INTERFERENCE BONE SCREW

(75) Inventors: Jordan A. Hoof, Phoenix, AZ (US); Kevin N. Baird, Phoenix, AZ (US); Derek J. Harper, Scottsdale, AZ (US)

(73) Assignee: Cayenne Medical, Inc., Scottsdale, AZ (US)

( * ) Notice: Subject to any disclaimer, the term of this patent is extended or adjusted under 35 U.S.C. 154(b) by 1330 days.

(21) Appl. No.: 12/363,571

(22) Filed: Jan. 30, 2009

(65) Prior Publication Data

US 2009/0198288 A1    Aug. 6, 2009

Related U.S. Application Data

(60) Provisional application No. 61/025,250, filed on Jan. 31, 2008.

(51) Int. Cl.
*A61B 17/04*  (2006.01)
*A61B 17/86*  (2006.01)
*A61F 2/08*   (2006.01)
*A61B 17/88*  (2006.01)

(52) U.S. Cl.
CPC ........... *A61B 17/864* (2013.01); *A61B 17/8615* (2013.01); *A61B 17/8635* (2013.01); *A61F 2/0811* (2013.01); *A61B 17/8605* (2013.01); *A61B 17/861* (2013.01); *A61B 17/888* (2013.01); *A61F 2002/0858* (2013.01); *A61F 2002/0882* (2013.01)
USPC .............................. 606/321; 606/76; 606/309

(58) Field of Classification Search
None
See application file for complete search history.

(56) References Cited

U.S. PATENT DOCUMENTS

| 3,454,070 | A | * | 7/1969 | Phipard, Jr. .................. 411/168 |
| 4,927,421 | A |   | 5/1990 | Goble et al. |
| 5,122,146 | A | * | 6/1992 | Chapman et al. ............. 606/102 |
| 5,236,457 | A | * | 8/1993 | Devanathan .................. 128/898 |
| 5,370,696 | A | * | 12/1994 | Jamison et al. ............... 623/23.6 |
| 5,456,685 | A | * | 10/1995 | Huebner ....................... 606/321 |

(Continued)

FOREIGN PATENT DOCUMENTS

WO    WO 9609014 A1 *   3/1996

OTHER PUBLICATIONS

Kurtz et al., PEEK Biomaterials in Trauma, Orthopedic, and Spinal Implants, Biomaterials 28, 2007, 4845-4869.*

(Continued)

*Primary Examiner* — Andrew Yang
(74) *Attorney, Agent, or Firm* — Donald E. Stout; Stout, Uxa & Buyan, LLP

(57) ABSTRACT

A biocompatible interference screw for soft tissue or bone-to-bone fixation comprises a screw body extending from a screw head to a distal tip of the screw. The screw body has an outer surface, and comprises polyether-ether-ketone (PEEK) material. Advantageously, the body outer surface has a textured surface finish for substantially improving pull-out strength of the interference screw. The textured surface finish is textured, in preferred embodiments, with a minimum of approximately 16 micro inches of surface roughness. The screw head comprises a tapered square keyhole for receiving a distal end of a driver instrument. The screw comprises a series of threads, which have a relatively smooth profile, in order to prevent graft tissue laceration as the screw is being inserted. The distal tip of the screw body comprises a narrow tip, and a distal end of the screw body is angled inwardly toward the narrow distal tip.

20 Claims, 3 Drawing Sheets

(56) References Cited

U.S. PATENT DOCUMENTS

| | | | |
|---|---|---|---|
| 6,030,162 A * | 2/2000 | Huebner | 411/413 |
| 6,565,573 B1 * | 5/2003 | Ferrante et al. | 606/62 |
| 6,786,909 B1 | 9/2004 | Dransfeld et al. | |
| 2005/0071013 A1 | 3/2005 | Zubok et al. | |
| 2005/0107800 A1 | 5/2005 | Frankel et al. | |
| 2005/0228388 A1 | 10/2005 | Brodke et al. | |
| 2007/0053765 A1 | 3/2007 | Warnick et al. | |
| 2007/0225785 A1 | 9/2007 | Park et al. | |
| 2008/0058939 A1 * | 3/2008 | Hughes et al. | 623/17.15 |
| 2009/0024174 A1 * | 1/2009 | Stark | 606/321 |

OTHER PUBLICATIONS

International Search Report and Written Opinion for corresponding PCT Application No. PCT/US09/32704.

\* cited by examiner

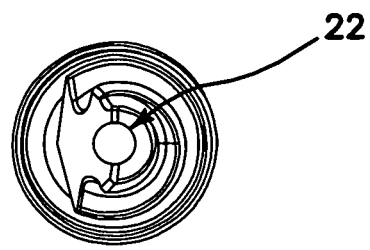
FIG. 3B
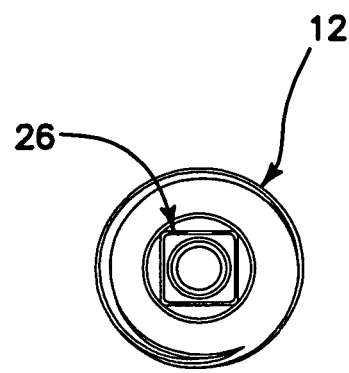
FIG. 3C
FIG. 4A
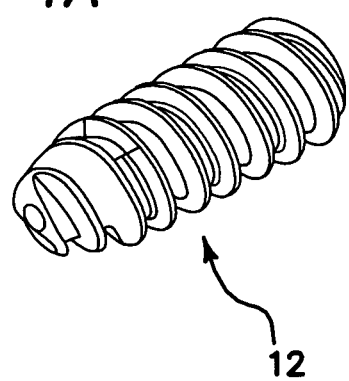
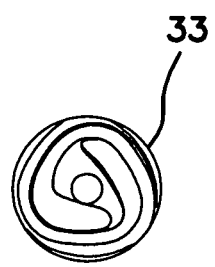
FIG. 4C
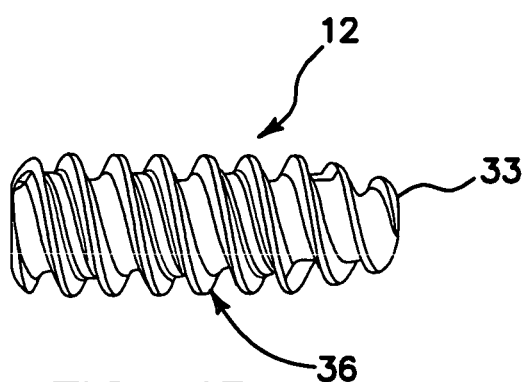
FIG. 4B

SELF-TAPPING BIOCOMPATIBLE INTERFERENCE BONE SCREW

This application claims the benefit under 35 U.S.C. 119(e) of the filing date of Provisional U.S. Application Ser. No. 61/025,250, entitled Self Tapping Biocompatible Interference Bone Screw, filed on Jan. 31, 2008, which application is expressly incorporated herein by reference, in its entirety.

BACKGROUND OF THE INVENTION

The present invention relates to soft tissue or bone-to-bone fixation devices, and more particularly to those comprised from the biocompatible polymer polyether-ether-ketone (PEEK).

Current biocompatible polymeric screws, such as those comprised of poly-1-lactide acid (PLLA) or poly-lactide acid (PLA), lack the durability to be inserted into cancellous bone without the additional step of manually tapping the implant site intended to receive the bone screw with a surgical bone tap. Though screws created from these materials possess the desired characteristics of radiolucency and MRI compatibility, the additional procedural step of tapping is often described as difficult, and translates into increased operating time.

There are relatively few tissue fixation devices in use in the orthopedics industry which are fabricated of PEEK, and there are no implantable PEEK bone screws available on the market. Within the industry, the trend is away from polymer-based and toward composite interference screws. For example, the thinking in the industry is that PEEK interference screws would have a higher likelihood of loosening and, thus, a relatively low pull-out strength, and they are thus disfavored for this type of application.

A typical application for bone screws such as the one described herein is in the reconstruction of the anterior cruciate ligament (ACL). This procedure is performed either with a soft-tissue or a bone-patellar-tendon-bone (BPTB) graft, currently considered to be the "gold standard" of ACL reconstruction procedures by many orthopedic surgeons. It is intended that the disclosed fixation implant is packaged sterile and used in conjunction with a reusable driver.

Current non-metallic interference screws pose several challenges for the patients who have them implanted and for the surgeons who utilize them. These challenges include, for example, a lack of circulation in bone and therefore slow or no absorption of bioabsorbables; weak tips, fracturing, and thread blunting; a requirement of tapping bone prior to insertion, as discussed above; and tendency of non-metallic screws to pull out of the bone site due to applied loading during therapy or recovery.

There are currently many different interference screws marketed for soft tissue or bone-tendon-patellar-bone ACL reconstruction. A bioabsorbable screw available from ARTHREX is indicated for use in both types of reconstruction and is comprised of PLLA. The blunt threads of the ARTHREX screw facilitate its use with soft tissue grafts by avoiding the problem of tissue laceration that could occur with sharper threads. However, because of these blunt threads, the ARTHREX Biointerference and Biocomposite Interference Screw Instructions for Use (IFU) state: "Prepare screw entrance insertion point using either the tap, dilator, or notcher. (Use only a dilator or notcher for the Round Delta Bio-Interference Screw.)".

The DePuy Mitek Biocryl screw is a composite made from the osteoconductive ceramic tricalcium phosphate (TCP) and polylactic acid (PLA). The DePuy Mitek Milagro screw is a composite made from the osteoconductive ceramic tricalcium phosphate (TCP) and poly(lactic-co-glycolic acid) (PLGA). These screws require a starter tap to "help screw engage in cortical bone." The Mitek IFU for both screws states: "Pre-tapping is necessary when inserting the interference screw into hard cortical bone with bonetendon grafts. The starter tap should be used no more than three to four full turns. Advancing the starter tap further may jeopardize fixation integrity."

Fixation strengths of interference screws are comparable between similarly sized screws across brands and product offerings. Many, if not all, bioabsorbable or biocomposite screws require a separate tapping procedure to prepare the implant site for screw insertion in harder bone to prevent damaging the screw. Many other screws require the use of a notcher or dilator to prepare the insertion site for the screw. Avoidance of such additional preparatory steps at the implantation site would be a significant advantage to practitioners in this medical field.

SUMMARY OF THE INVENTION

The disclosed invention is a cannulated, molded, self-tapping PEEK bone screw that has the attributes of radiolucency and MRI compatibility. The durability of the PEEK material and the screw's narrow, chamfered tip gives it the ability to easily grasp purchase into the bone at the site of implantation. Testing has shown that with the design disclosed herein, it is unnecessary to tap the bone prior to inserting the screw. PEEK is a material that has had long standing application within the implant industry in the medical field.

In conjunction with the screw, a reusable insertion and positioning tool allows the surgeon to drive the screw into place while guiding it over a flexible nitinol guide wire. The screw is inserted into the bone by the driver in a clockwise rotation. The interference fit between the bone graft and tunnel wall occurs as the thread of the screw forwardly propels the screw body into the bone. The minor diameter of the screw acts as the interfering body between either the soft-tissue or bone graft and the tunnel wall essentially press fitting the bodies together and preventing the graft from sliding through the tunnel without significant required force. In the case of BPTB procedures, the screw is inserted against the boney side of the BPTB graft, allowing the soft tissue side on the alternate lateral half of the BPTB graft to osteointegrate within the surrounding bone. Aside from the body of the screw providing a pure interference fit between the bone tunnel and graft, the screw's thread provides additional fixation of the graft by essentially tacking it into position within the bone tunnel. Depending on the cut depth of the thread (the difference between the major and minor radius of the screw) the amount of bone purchase the screw thread has grasped can be controlled.

The use of the device is straightforward, eliminating potential for confusion that may arise when using other bone screw fixation technologies. No additional accessories or steps are required other than the screw, driver, and optional guide wire. The only step required in preparation for graft fixation is to locate and drill tunnels within the femur and tibia.

The narrow tip of the inventive interference screw allows it to be used in most situations without requiring dilation or notching at the implant site. Furthermore, the durability of the PEEK material in combination with its angled tip design allows it to be implanted into harder bone without requiring the use of a tap. The tapless/notchless screw design was verified by measuring the ease of insertion during implantation into porcine bone, having a higher density than human bone. The predicate device chosen for the present device validation before the FDA required the use of a separate tapping step in order perform its installation whereas the inventive screw requires no additional preparatory steps at the implantation site More particularly, in one aspect of the invention, there is provided a biocompatible interference screw for soft tissue or bone-to-bone fixation, which comprises a preferably rounded screw head for permitting a user to insert the screw to a desired location within a patient's body. The inventive screw further comprises a screw body extending from the screw head to a distal tip of the screw. The screw body has an outer surface, and comprises polyether-ether-ketone (PEEK) material. Advantageously, the body outer surface has a textured surface finish for substantially improving pull-out strength of the interference screw. The textured surface finish is textured, in preferred embodiments, with a minimum of approximately 16 micro inches of surface roughness, and is bead blasted. The screw head comprises a tapered square keyhole for receiving a distal end of a driver instrument. The screw comprises a series of threads, which have a relatively smooth profile, in order to prevent graft tissue laceration as the screw is being inserted. The distal tip of the screw body preferably comprises a narrow tip, and a distal end of the screw body is preferably angled inwardly toward the narrow distal tip.

Additionally, a distal portion of the screw body, comprising approximately one-half of a total length of the screw body, has a tapered configuration. The screw body further preferably comprises a transitioning thread cut adjacent to the screw head. A cannulation extends through the screw body for receiving a guide wire.

In a modified embodiment of the inventive screw, a distal end of the screw body has a trilobular configuration.

In another aspect of the invention, there is provided a system for performing soft tissue or bone-to-bone fixation, which comprises a biocompatible interference screw comprising a screw body fabricated of PEEK material and having a threaded outer surface. The screw body outer surface has a textured surface finish, wherein the textured surface finish on the screw body outer surface is textured with a minimum of approximately 16 micro inches of surface roughness. The system additionally comprises a driver comprising a handle and an attached shaft distal to the handle. The handle and attached shaft have a cannulation therethrough for receiving a guide wire. The system preferably also comprises a guide wire.

The aforementioned handle comprises a locking thumb wheel for locking and unlocking a guide wire in place within the cannulation. The shaft has a distal tip configured to mate with a head of the screw body, for inserting the screw into a desired body location and driving the screw in place within bone at the desired body location. The screw body also has a cannulation therethrough for receiving a guide wire.

The invention, together with additional features and advantages thereof, may best be understood by reference to the following description taken in conjunction with the accompanying illustrative drawing.

BRIEF DESCRIPTION OF THE DRAWINGS

FIG. 3B is a distal end view of the screw of FIG. 3A;

FIG. 3C is a proximal end view of the screw of FIG. 3A;

FIG. 4A is an isometric view of a modified embodiment of the screw illustrated in FIG. 1;

FIG. 4B is a plan view of the screw of FIG. 4A;

FIG. 4C is a distal end view of the screw of FIG. 4B; and

DESCRIPTION OF THE PREFERRED EMBODIMENT

Figure 1:
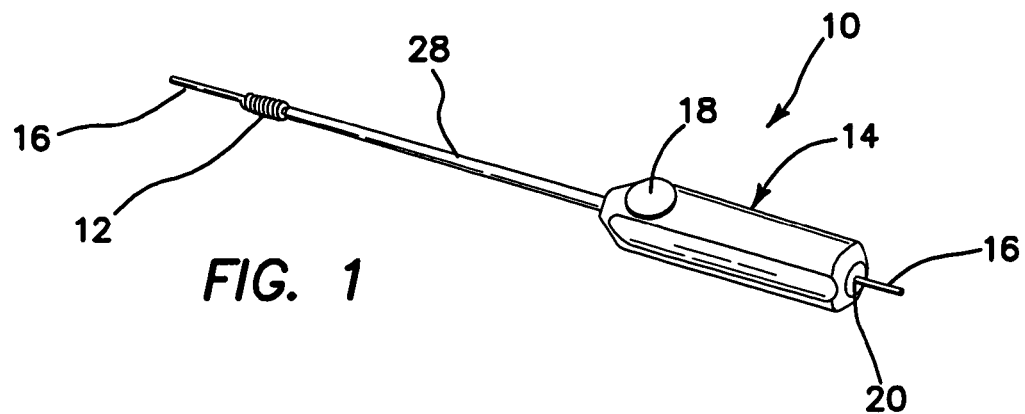
FIG. 1 is an isometric view of an interference screw, driver, and guide wire constructed and assembled in accordance with the principles of the present invention.
Figure 2:
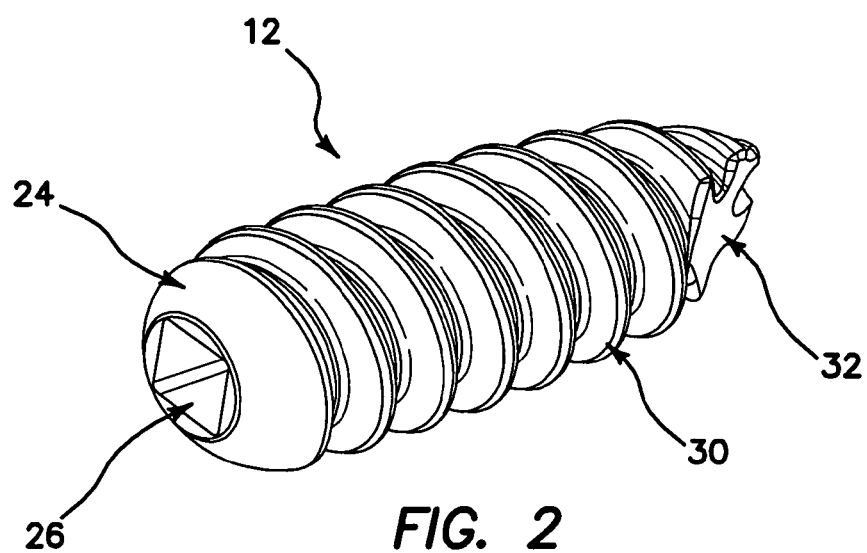
FIG. 2 is an isometric view of the screw illustrated in FIG. 1.

Referring now more particularly to the drawings, there is shown in FIG. 1 an interference screw anchoring system 10, which comprises an interference screw 12, a driver 14, and a guide wire 16, along which the driver 14 and interference screw 12 may be guided to a desired operative site.

The inventive interference screw 12 is intended for the bone-patellar tendon-bone reconstruction of the ACL, but may be used in other applications as well. During an ACL reconstruction procedure, BPTB grafts are fixed to the femur and tibia, utilizing the inventive interference screw 12. BPTB grafts are typically harvested from the patient's ipsilateral leg, but cadaveric grafts are also acceptable. The interference screw is packaged sterile, and is designed to provide compression of a BPTB graft within the femoral and tibial tunnels at the procedural site. The driver 14, and other system components comprising the instrument set 10 are designed to be reusable. A disposable kit provided with the system 10 includes the guide wire 16 and other disposable elements of the system.

In preferred embodiments, the interference screw 12 may be offered in up to 18 different sizes. The labeled diameters may range from 7 mm to 12 mm. The labeled lengths of the implants may be 20 mm, 25 mm, and 30 mm. The interference screw 12 is preferably made of PEEK OPTIMA® (Polyetheretherketone) material, which is a biocompatible polymer. PEEK OPTIMA® material is supplied by Invibio Inc. Biocompatibility data for PEEK OPTIMA® material exists at Invibio Inc. Of course, other equivalent or similar biocompatible materials may be substituted for this specific preferred material.

Figure 5:
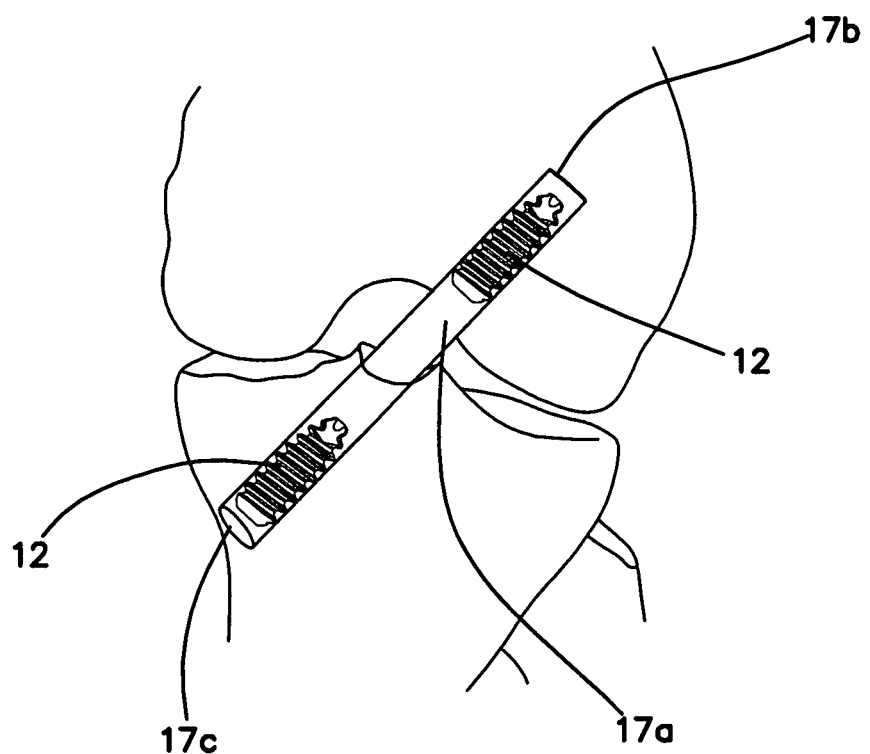
FIG. 5 is an illustration of a preferred application for the inventive screw anchors.

In operation, and with reference to FIG. 5 as well as to FIG. 1, a BPTB graft 17a is harvested and prepared (sutures are attached to each end of the graft) according to standard procedures, the torn ACL is removed, and femoral and tibial holes 17b, 17c, respectively, are drilled to the appropriate size, in procedures which are known in the art, and as are described, for example, in commonly assigned U.S. patent application Ser. No. 11/923,526, herein expressly incorporated by reference, in its entirety. Next the graft is passed into the joint, starting inferiorly at the site of the tibial tunnel 17c. This is done by threading the sutures placed at each of the bone block ends of the graft, in the top end of the graft, through the guide pin eyelet and pulling upwardly through the tibial and femoral tunnels into its desired position. The graft is guided by the sutures through the tibial drill hole, into the central portion of the joint, and finally into the femoral drill hole, using a pin puller. The interference screw 12 is then used to secure the graft in place, both within the femoral and tibial tunnels.

The interference screw installation driver 14 features a locking thumb wheel 18, which is used to clamp a nitinol guide wire 16 for insertion between the graft bone plug and tunnel wall. If desired, the tip of the driver 14 may be used to create a pilot insertion point for the interference screw between the graft and the drill tunnel. The nitinol guide wire 16 is inserted through a cannulated portion 20 of the driver, and the thumb wheel 18 is rotated in a clockwise direction to lock the guide wire 16 into place. In this manner, the driver 14 can be used to push the guide wire 16 between the graft and the tunnel wall.

Referring now, as well, to FIGS. 2 and 3A-3C, the interference screw 12 includes a guide wire cannulation 22 (FIG. 3B) through the center thereof, which is preferably one of two different diameters, either 1.2 mm or 2.0 mm. The smaller cannulation diameter of 1.2 mm is utilized with screw diameters of 7 mm or 8 mm, and the larger cannulation diameter of 2.0 mm is utilized for screw diameters of 9 mm through 12 mm, taking advantage of a larger diameter cannulation and guide wire for increased screw insertion stiffness. The guide wire is inserted through the cannulated portion 20 of the driver 14, and the thumb wheel 18 is tightened to lock the guide wire into place within the cannula. The guide wire is then positioned as desired within the femoral tunnel. If necessary, at this juncture, the screw insertion point is prepared by using the tip of the driver 14. The thumb wheel 18 is loosened, and the back of the driver 14 is tapped to push the driver tip at the distal end of the shaft 28 between the bone plug and the tunnel, forming an insertion point for the screw tip. The thumb wheel 18 is then loosened, and the driver 14 is removed from the operative site, leaving the guide wire in place in the tunnel.

The first interference screw 12 is mounted onto the driver 14 and installed between the drill tunnel and graft bone plug. The nitinol guide wire 16 is used to guide the screw into proper position by passing it through the central cannulation 20 of the driver and the cannulation 22 of the screw. Installation is complete when the screw is flush with the perimeter of the drill tunnel. The screw 12 is driven into the bone by rotating the driver 14 clockwise over the guide wire until the screw is fully inserted within the drill hole. Then, the driver and guide wire are removed from the operative site and the insertion procedure is repeated on the tibial side to complete graft fixation.

Figure 3A:
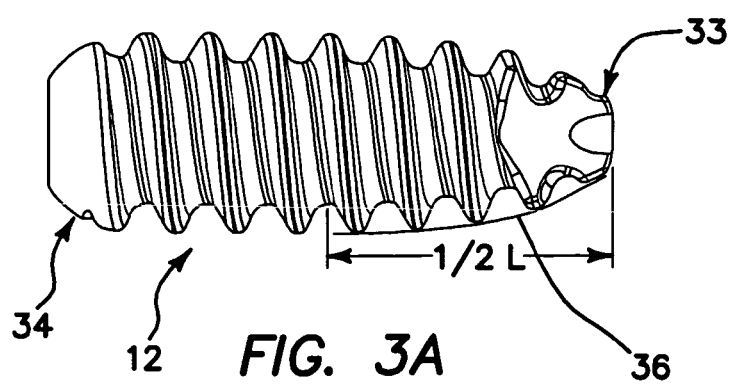
FIG. 3A is a plan view of the screw of FIG. 2.

The screw 12 comprises, in the illustrated embodiment, a rounded head 24, a tapered square keyhole 26 for receiving the distal end of a shaft 28 of the driver 14, and a smooth thread profile 30. A distal end 32 of the screw 12 is angled inwardly in a distal direction, as shown, to form a narrow tip 33. An additional feature of the screw 12 comprises a transitioning thread cut 34. The distal portion, approximately one-half of the total length, of the screw body 36 is tapered toward the narrow tip 33, as shown in FIG. 3A.

The screw pitch, tip angle and thread depth are variables that change according to the screw size. The thread cut profile is consistent across each size and varies only by the depth to which it is cut. One particular unique and advantageous feature of the inventive screw 12 is its modified surface finish. The outer surface of the screw is textured with a minimum of 16 micro inches of surface roughness. Texturing the screw surface increases its overall surface area, which the inventors have found improves its tissue adhesion and osteointegration, and thus substantially hastens recovery time of the rehabilitating patient. Of equal importance, the textured surface finish increases the coefficient of friction between the screw and adjacent bone. This issue is of importance since it has historically been believed in the industry that interference screws made of PEEK material would be insufficient for BPTB repair because of the concern of screw loosening that might occur during cyclic loading. The inventors have determined that texturing the screw substantially and surprisingly increases the amount of torque required to insert it within the bone tunnel against the bone plug. Higher insertion torques have been correlated with higher pullout strengths in BPTB grafts. Furthermore, a screw that requires more torque to insert will require an equally higher amount of torque to facilitate its removal by loosening. Therefore, the inventive textured screw is substantially more resilient to the loosening phenomenon during cyclic loading than one that is untextured. The pullout forces of textured vs. untextured PEEK screws were compared by the assignee in an in vitro porcine model. At a 95% level of confidence, the textured PEEK screws were found to have a significantly higher mean pullout force than untextured PEEK screws, on the order of approximately 20% or more. On average, of the samples tested, textured PEEK screws had a mean pullout force of 713 N compared to a mean pullout force of 508 N for untextured screws. Therefore, it can be concluded that texturing the screw significantly increases the pullout force of the graft from the interference fixation point. One final feature that texturing the screws offers is the provision of desirable audible feedback to the operating physician. Untextured screws are silent during insertion into the implantation site. Texturing the screw surface causes the screw to audibly "squeak" during insertion, a feature that many physicians rely on to ensure that the screw is actually providing a tight fit relative to their chosen bone-plug/tunnel/screw sizing scheme. A preferred texturing technique involves utilizing bead blasting equipment.

Another innovative feature of screw 12 of the present invention is its tapless insertion. The durability of the PEEK material compared to other biocompatible polymers such as PLA, PLLA or TCP is much higher. Using PEEK instead of a weaker material avoids the problem of thread deformation or tip fracturing experienced with screws composed from other biocompatible polymers. The durability of the PEEK material, combined with the screw body's narrow tip 33 and angled distal tip 32 design allows these features to function as an "easy-start" for the screw, which facilitates its insertion into denser bone without a separate tapping step required by screws of weaker materials. The self-tapping features of the screw were verified in comparison to a predicate device in an in vitro porcine medium. The smooth thread profile 30 of the screw prevents graft tissue laceration as it is being inserted. The angled tip 32 also functions to create a wider guide wire insertion point since the cannulation 22 is cut at the same relative angle as the tip. This feature allows easier insertion of the guide wire through the cannulation than screws that have an tip that is not angled.

The rounded screw head 24 allows the practitioner to fully insert the screw through bone surfaces at a variety of planar angles, thereby limiting the likelihood that the final screw position will be prone. The transitioning thread cut 34 and rounded head 24 is a modified variant of a pure "round head" type interference screw and a "full thread" interference screw. The square keyhole 26 of the screw allows higher torque to be applied to the screw than other geometries. This feature is slightly tapered as is the driver tip to allow a perfect fit between screw and driver and limits the impact of manufacturing variability on driver-screw fit.

The tapered screw body 36 transition to full diameter occurs over the first one-half of the total screw length. This allows the screw to be more easily inserted, and more evenly distributes the stresses at the bone-plug/screw junction under tensile loading, preventing internal stress concentration points depending on the orientation of the screw in fixation.

FIGS. 4A-4C illustrate a modified embodiment of the inventive screw 12. This embodiment is of a trilobular design, a design commonly found in self-tapping screws for plastics. As illustrated, three distinct lobes of the screw form a triangular tip that facilitates cutting into the bone. The trilobular tip transitions proximally into the more cylindrical body 36 of the screw, thus allowing appropriate fixation at any angle around the circumference of the screw.

Accordingly, although an exemplary embodiment of the invention has been shown and described, it is to be understood that all the terms used herein are descriptive rather than limiting, and that many changes, modifications, and substitutions may be made by one having ordinary skill in the art without departing from the spirit and scope of the invention, which is to be limited only in accordance with the following claims.

What is claimed is:

1. A biocompatible interference screw for soft tissue or bone-to-bone fixation, comprising:
    a screw head for permitting a user to insert the screw to a desired location within a patient's body; and
    a screw body extending from said screw head to a distal tip of the screw, said screw body having an outer surface;
    said screw body comprising polyether-ether-ketone (PEEK) material, and said outer surface having a textured non-metallic PEEK surface finish for substantially improving pull-out strength of said interference screw, wherein said non-metallic textured surface finish also comprises PEEK material and is textured with a predetermined minimum level of surface roughness, wherein said predetermined minimum level of surface roughness for said textured surface finish is approximately 16 micro inches of surface roughness.

2. The interference screw as recited in claim 1, wherein said screw head is rounded in configuration.

3. The interference screw as recited in claim 1, wherein said screw further comprises a tapered square keyhole in said screw head for receiving a distal end of a driver instrument.

4. The interference screw as recited in claim 1, wherein said screw comprises a series of threads, said threads having a relatively smooth profile.

5. The interference screw as recited in claim 1, wherein said distal tip comprises a narrow tip, and a distal end of the screw body is angled inwardly toward said distal tip.

6. The interference screw as recited in claim 1, wherein a distal portion of said screw body has a tapered configuration.

7. The interference screw as recited in claim 6, wherein said tapered distal portion comprises approximately one-half of a total length of said screw body.

8. The interference screw as recited in claim 1, wherein said textured surface finish is bead blasted.

9. The interference screw as recited in claim 1, wherein said screw body further comprises a transitioning thread cut adjacent to said screw head.

10. The interference screw as recited in claim 1, and further comprising cannulation extending through said screw body for receiving a guide wire.

11. The interference screw as recited in claim 1, wherein a distal end of the screw body has a trilobular configuration.

12. The interference screw as recited in claim 1, wherein the screw body is sheathless.

13. The interference screw as recited in claim 1, wherein the screw body is uncoated.

14. A system for performing soft tissue or bone-to-bone fixation, comprising:
    a biocompatible interference screw comprising a screw body fabricated of PEEK material and having a threaded outer surface; said screw body outer surface having a non-metallic textured surface finish also comprising PEEK material, wherein the textured surface finish on said screw body outer surface is textured with a minimum of approximately 16 micro inches of surface roughness;
    a driver comprising a handle and an attached shaft distal to said handle, said handle and attached shaft having a cannulation therethrough for receiving a guide wire.

15. The system as recited in claim 14, and further comprising a guide wire.

16. The system as recited in claim 14, wherein said handle further comprises a locking thumb wheel for locking and unlocking a guide wire in place within said cannulation.

17. The system as recited in claim 14, wherein said shaft has a distal tip configured to mate with a head of said screw body for inserting said screw into a desired body location and driving said screw in place within bone at said desired body location.

18. The system as recited in claim 14, wherein said screw body also has a cannulation therethrough for receiving a guide wire.

19. The system as recited in claim 14, wherein the screw body is sheathless.

20. The system as recited in claim 14, wherein the screw body is uncoated.

* * * * *